(12) United States Patent
Ziegler et al.

(10) Patent No.: US 7,906,132 B2
(45) Date of Patent: Mar. 15, 2011

(54) ANTI-INFECTIOUS, BIOCOMPATIBLE TITANIUM COATING FOR IMPLANTS, AND METHOD FOR THE PRODUCTION THEREOF

(75) Inventors: Gunter Ziegler, Eckersdorf (DE); Hans Gollwitzer, Munich (DE); Frank Heidenau, Pegnitz (DE); Wolfram Mittelmeier, Bad Doberan (DE); Frauke Stenzel, Herrnburg (DE)

(73) Assignee: Biocer-Entwickslung GmbH, Bayreuth (DE)

( * ) Notice: Subject to any disclaimer, the term of this patent is extended or adjusted under 35 U.S.C. 154(b) by 650 days.

(21) Appl. No.: 10/527,921

(22) PCT Filed: Sep. 17, 2003

(86) PCT No.: PCT/EP03/10334
§ 371 (c)(1), (2), (4) Date: Sep. 30, 2005

(87) PCT Pub. No.: WO2004/026346
PCT Pub. Date: Apr. 1, 2004

(65) Prior Publication Data
US 2006/0161256 A1    Jul. 20, 2006

(30) Foreign Application Priority Data
Sep. 17, 2002   (DE) .................................. 102 43 132

(51) Int. Cl.
*A01N 25/08* (2006.01)
(52) U.S. Cl. ...................................................... 424/409
(58) Field of Classification Search ................... 424/422, 424/423, 425; 623/11.11; 427/2.1, 2.24
See application file for complete search history.

(56) References Cited

U.S. PATENT DOCUMENTS

| | | |
|---|---|---|
| 2,040,806 A | 5/1936 | Felgi |
| 2,521,713 A | 9/1950 | Goetz |
| 2,785,153 A | 3/1957 | Locke et al. |
| 3,590,486 A | 7/1971 | Brenner et al. |
| 3,864,139 A | 2/1975 | Heller |
| 4,027,393 A | 6/1977 | Ellis et al. |
| 4,113,660 A | 9/1978 | Abe et al. |
| 4,206,516 A | 6/1980 | Pilliar |
| 4,252,525 A | 2/1981 | Child |
| 4,263,681 A | 4/1981 | Notton |
| 4,291,125 A | 9/1981 | Greatbatch |

(Continued)

FOREIGN PATENT DOCUMENTS
DE    10243132 A1    4/2004
(Continued)

OTHER PUBLICATIONS

Tseng, I-H. et al., Photoreduction of $CO_2$ using sol-gel derived titania and titania-supported copper catalysts, Applied Catalysis B: Environmental 37 (2002), pp. 37-48.

(Continued)

*Primary Examiner* — Carlos A Azpuru
(74) *Attorney, Agent, or Firm* — David W Maher; TechLaw LLP

(57) ABSTRACT

The present invention relates to a method for the preparation of a biocompatible metal ion-containing titanium oxide coating on an implant wherein the metal ions can be eluted under physiological conditions and are homogeneously dispersed within the coating, as well as to an implant which can be prepared according to the method of the present invention.

30 Claims, 1 Drawing Sheet

U.S. PATENT DOCUMENTS

| | | | |
|---|---|---|---|
| 4,476,590 A | 10/1984 | Scales et al. | |
| 4,570,271 A | 2/1986 | Sump | |
| 4,592,920 A | 6/1986 | Murtfeldt | |
| 4,615,705 A * | 10/1986 | Scales et al. | 424/422 |
| 4,731,198 A | 3/1988 | Watanabe et al. | |
| 4,790,851 A | 12/1988 | Suire et al. | |
| 4,834,756 A | 5/1989 | Kenna | |
| 4,849,223 A * | 7/1989 | Pratt et al. | 424/409 |
| 4,871,366 A | 10/1989 | Von Recum et al. | |
| 4,906,466 A * | 3/1990 | Edwards et al. | 424/421 |
| 4,954,476 A | 9/1990 | Hums | |
| 4,976,738 A | 12/1990 | Frey et al. | |
| 5,019,096 A | 5/1991 | Fox, Jr. et al. | |
| 5,147,686 A * | 9/1992 | Ichimura et al. | 427/217 |
| 5,169,597 A | 12/1992 | Davidson et al. | |
| 5,219,363 A | 6/1993 | Crowninshield et al. | |
| 5,378,268 A | 1/1995 | Wolf et al. | |
| 5,480,438 A | 1/1996 | Arima et al. | |
| 5,486,225 A | 1/1996 | Dye et al. | |
| 5,531,716 A | 7/1996 | Luzio et al. | |
| 5,612,049 A | 3/1997 | Li et al. | |
| 5,688,492 A * | 11/1997 | Galley et al. | 424/49 |
| 5,716,400 A | 2/1998 | Davidson | |
| 5,753,251 A | 5/1998 | Burrell et al. | |
| 5,782,910 A | 7/1998 | Davidson | |
| 5,820,918 A | 10/1998 | Ronan et al. | |
| 5,855,612 A | 1/1999 | Ohthuki et al. | |
| 5,873,904 A | 2/1999 | Ragheb et al. | |
| 5,976,169 A | 11/1999 | Imran | |
| 5,984,965 A | 11/1999 | Knapp et al. | |
| 5,985,308 A | 11/1999 | Burrell et al. | |
| 6,013,106 A | 1/2000 | Tweden et al. | |
| 6,017,553 A | 1/2000 | Burrell et al. | |
| 6,039,762 A | 3/2000 | McKay | |
| 6,063,442 A | 5/2000 | Cohen et al. | |
| 6,093,414 A * | 7/2000 | Capelli | 424/405 |
| 6,264,936 B1 | 7/2001 | Sawan et al. | |
| 6,267,782 B1 | 7/2001 | Ogle et al. | |
| 6,296,863 B1 | 10/2001 | Trogolo et al. | |
| 6,312,472 B1 | 11/2001 | Hall et al. | |
| 6,313,064 B1 | 11/2001 | Miyafuji et al. | |
| 6,344,057 B1 | 2/2002 | Rabbe et al. | |
| 6,350,408 B1 | 2/2002 | Dye et al. | |
| 6,368,356 B1 | 4/2002 | Zhong et al. | |
| 6,387,446 B1 | 5/2002 | Lobmann et al. | |
| 6,482,444 B1 | 11/2002 | Bellantone et al. | |
| 6,582,715 B1 | 6/2003 | Barry et al. | |
| 6,585,767 B1 | 7/2003 | Holley et al. | |
| 6,596,401 B1 | 7/2003 | Terry et al. | |
| 6,638,634 B2 | 10/2003 | Miyasaka | |
| 6,641,831 B1 | 11/2003 | Schierholz | |
| 6,663,634 B2 | 12/2003 | Ahrens et al. | |
| 6,663,877 B1 | 12/2003 | Appleton et al. | |
| 6,689,302 B2 | 2/2004 | Reisdorf et al. | |
| 6,706,795 B1 | 3/2004 | Garti et al. | |
| 6,716,895 B1 | 4/2004 | Terry | |
| 6,730,127 B2 | 5/2004 | Michelson | |
| 6,761,984 B2 | 7/2004 | Anzaki et al. | |
| 6,846,578 B2 | 1/2005 | Kumacheva et al. | |
| 6,916,480 B2 | 7/2005 | Anderson et al. | |
| 6,984,392 B2 * | 1/2006 | Bechert et al. | 424/422 |
| 7,018,411 B2 | 3/2006 | Gosheger et al. | |
| 2001/0002994 A1 * | 6/2001 | Masuhara et al. | 424/49 |
| 2001/0036530 A1 | 11/2001 | Noda et al. | |
| 2001/0053937 A1 | 12/2001 | Johnson et al. | |
| 2002/0099449 A1 | 7/2002 | Speitling | |
| 2002/0169066 A1 | 11/2002 | Cassidy et al. | |
| 2003/0167878 A1 | 9/2003 | Al-Salim et al. | |
| 2003/0175321 A1 | 9/2003 | Sapieszko et al. | |
| 2003/0180344 A1 | 9/2003 | Wise et al. | |
| 2003/0181973 A1* | 9/2003 | Sahota | 623/1.15 |
| 2004/0043153 A1 | 3/2004 | Okuhama et al. | |
| 2004/0111159 A1 | 6/2004 | Pope et al. | |
| 2004/0121451 A1 | 6/2004 | Moritz et al. | |
| 2004/0132603 A1 | 7/2004 | Narhi et al. | |
| 2005/0014151 A1 | 1/2005 | Textor et al. | |
| 2005/0246032 A1 | 11/2005 | Bokros et al. | |
| 2006/0020346 A1 | 1/2006 | Hunter et al. | |
| 2006/0051544 A1 | 3/2006 | Goldmann | |
| 2006/0058882 A1 | 3/2006 | Haines | |
| 2006/0079953 A1 | 4/2006 | Gregorich et al. | |
| 2006/0093729 A1 | 5/2006 | Marx et al. | |
| 2006/0161256 A1 | 7/2006 | Ziegler et al. | |
| 2007/0077267 A1 | 4/2007 | Molz, IV et al. | |
| 2007/0093911 A1 | 4/2007 | Fricke et al. | |
| 2008/0046091 A1 | 2/2008 | Weiss et al. | |
| 2008/0050699 A1 | 2/2008 | Zhang et al. | |

FOREIGN PATENT DOCUMENTS

| | | |
|---|---|---|
| EP | 0 222 717 A2 | 5/1987 |
| EP | 0222717 A3 | 5/1987 |
| EP | 0222717 A2 | 6/1987 |
| EP | 0 409 810 A2 | 1/1991 |
| EP | 0409810 A2 | 1/1991 |
| EP | 0409810 A3 | 1/1991 |
| EP | 0642362 B1 | 3/1995 |
| EP | 0926256 B1 | 6/1999 |
| EP | 03770943.3 | 9/2003 |
| JP | 09249981 | 9/1997 |
| JP | 9249981 A | 9/1997 |
| WO | 9956800 A1 | 11/1999 |
| WO | 2004026346 A2 | 4/2004 |
| WO | 2006058906 A1 | 6/2006 |
| WO | 2007027794 A1 | 3/2007 |

OTHER PUBLICATIONS

Heidenau F., et al., "Structured porous titania as a coating for implant materials," Key Engineering Materials, 192-195:87-90 (2001).

Nablo, Brian J. et al., "Sol-Gel derived nitric-oxide releasing materials that reduce bacterial adhesion," J. Am. Chem. Soc., 123:9712-9713 (2001).

Peltola T., et al., "Effect of aging time of sol on structure and in vitro calcium phosphate formation of sol-gel-derived titania films," J Biomed Mater Res, 51:20-208 (2000).

Schenk-Meuser K., et al., "XPS analysis of sol-gel-generated mixed-oxide layers for biomedical application," Surface and Interface Analysis, 33:59-62 (2002).

Tseng. I-Hsiang et al., "Photoreduction of $CO_2$ using sol-gel derived titania and titiana-supported copper catalysts," Applied Catalysis B: Environmental, 37:37-48 (2002).

* cited by examiner

ANTI-INFECTIOUS, BIOCOMPATIBLE TITANIUM COATING FOR IMPLANTS, AND METHOD FOR THE PRODUCTION THEREOF

The present invention relates to a method for the preparation of a biocompatible titanium oxide coating containing metal ions on an implant wherein the metal ions can be eluted under physiological conditions and are homogenously distributed throughout the coating, as well as to an implant which can be prepared according to the method of the present invention.

BACKGROUND OF THE INVENTION AND PRIOR ART

Silver or silver-containing coatings for anti-infectious finishing of short-term implants, such as catheters, are conventional methods already used in the clinical field, and the anti-bacterial effect is known from the literature [1-3]. Up to now, the anti-bacterial effect of copper or copper ions, respectively, has been examined mainly using metallic films, i.e. pure copper surfaces [4]. A use of elementary copper as an admixture has been described for an anti-bacterial wall paint [5]. The elution of copper ions from copper-thiomolybdate complexes into the blood of rats has been described by Komatsu, et al. [6]. Copper-containing titanium oxide layers obtained by thermal oxidation of a copper-containing titanium alloy are disclosed in the Japanese Patent laid-open Nos. JP9118987 and JP9249981. This method does not comprise a true coating procedure or coatings, respectively, however, merely the surface of copper-containing titanium alloys is altered by means of an acid treatment. The French Patent Application FR2780417 describes a similar procedure but wherein the surface of the treated alloy is treated with an oxidizing mineral acid prior to oxidation to form a surface oxide layer. The preparation of biocompatible titanium oxide coatings from nanosuspensions, so-called sols, is known for example from [7] and [8].

In a clinical environment bacterial contaminations are a latent an unavoidable danger, particular in the surgical area, e.g. during operative interventions at a patient. Primarily due to the introduction of foreign objects (implants such as catheters, osteosynthesis plates, endoprostheses, etc.) a process occurs immediately following implantation which is called in the literature a "race for the surface" [11]. This refers to a competition between the body's own cells and the microorganisms introduced during the operation to populate the initially sterile surfaces of the implant. If the implant surface is initially colonized excessively by bacterial cells and a manifest infection occurs the immune mechanisms of the human body are induced, and the possibility arises that the implant is rejected. In most cases, implants colonized by bacteria must be removed to treat the infection since even high concentrations of effective antibiotics cannot achieved a complete eradication of adhering bacteria [12, 13]. If the implant surfaces are devised in a highly toxic manner, however, colonization by the body's own cells required for integration of the implant is inhibited at the same time. This effect is especially undesirable for long-term implants, such as hip joint endoprostheses. A colonization with vital body cells promotes the integration of the implant and impedes an infection.

Therefore it is an object of the present invention to provide a coating for implants which inhibits the growth of introduced microorganisms on these implants, particularly the growth of bacteria, and which subsequently provides a biocompatible surface for the body's own cells.

According to the present invention, this has been achieved by a method according to claim 1 and an implant which can be prepared according to this method. According to the invention, also the use of the implant for an implantation into patients is comprised. Other embodiments of the present invention become clear from the dependent claims and the following specification.

Specification

Figure 1:
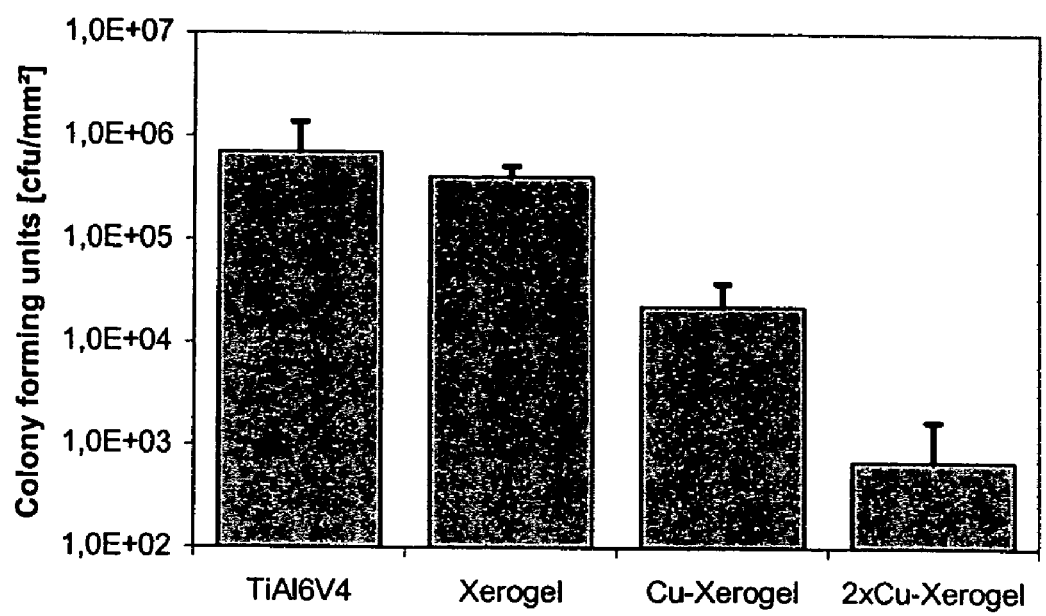
FIG. 1 shows the development of the cell number of *S. aureus* ATCC 25923 after 24 h of culture on various material surfaces.

According to the invention there is provided a method for the preparation of a biocompatible titanium oxide coating containing metal ions on an implant by which an implant can be prepared wherein the metal ions are released from the coating into the surroundings under physiological conditions and wherein the metal ions are homogenously dispersed throughout the coating.

According to the present invention implant is intended to mean a substrate suitable for implantation in a patient. Examples of implants are catheters, osteosynthesis material, endoprostheses, external/internal fixateurs, nails, screws, and/or wires, heart valves, artificial blood vessels and shunts, implants for facial/plastic surgery, middle ear implants, dental implants, etc.

According to the prior art, titanium oxide coatings are prepared by oxidation of titanium at increased temperatures or for example by plasma spray procedures. By these methods it is impossible to achieve a homogenous introduction of metal ions. For instance, by known physical coating procedures such as PVD (physical vapour deposition) the depositions formed on surfaces are not uniform but always islet-like resulting in a risk of local toxicity. In the method known from the prior art for the introduction of metals or metal ions into a matrix these have always been admixed to powders in the form of powders of the size of micrometers or salt-like compounds of the same size in a powder-metallurgical manner and dry pressed whereby an only inhomogeneous distribution of the material in the suspension and thus also in the finished material is achieved [9, 10].

In contrast, the present invention relates to a titanium oxide coating or an implant provided with a titanium oxide coating, respectively, wherein metal ions are contained in the coating which are distributed homogeneously throughout the coating and can be eluted under physiological conditions. The metal ions are present in the coating in a concentration that the coating initially is able to present an anti-microbial or anti-bacterial effect, respectively, due to the metal ions contained therein essentially without damaging the body's own cells. The ions are initially present in the coating in such a concentration that they are dissolved out under physiological conditions and are able to perform their anti-microbial effect at the surface of the coating.

Physiological and pathophysiological conditions according to the present invention are conditions which can be encountered in the surroundings of an implant implanted into a patient. According to the invention, this term comprises all body fluids contacting the implanted implant and also any other buffer solutions used as a substitute of body fluids such as a physiological saline, phosphate buffered saline (PBS) and the like.

After some time, the concentration in the coating decreases to a level that an anti-microbial or anti-bacterial effect, respectively, is no longer obtained, whereafter the remaining layer is perfectly compatible with the body's own cells. In this respect, the anti-bacterial effect additionally can be precisely dosed be regulating the composition of the layer. It can be reasonable for example to provide implants intended for implant bearings which are particularly prone to infections with a higher concentration of metal ions (e.g. medullary nails in the context of open bone fractures, external fixateur by means of Steinmann nails or pins in the case of osteomyelitis, temporary spacers for infected endoprostheses in the context of so-called exchange interventions at two different times (zweizeitige Wechseleingriffe)). However, the concentration of metal ions must not exceed a toxic concentration since otherwise damage of the host organism would occur. On the other hand, the level should not fall below the threshold concentration for the anti-bacterial effect until the bacteria introduced during implantation have been eliminated.

Generally, the concentrations of metal ions in the titanium oxide coating can preferably be 0.1-20% by weight with respect to the total coating, preferably 5-15% by weight, still more preferably 10-12% by weight.

According to the invention, titanium oxide essentially refers to titanium dioxide. According to the invention, however, also titanium oxide having other valences of titanium is comprised as well as mixtures of these with titanium dioxide as long as these titanium oxides do not show a detrimental effect with respect to biocompatibility and toxicity.

The thickness of the titanium oxide coating according to the invention is in the range of several hundreds of nanometers, preferably about 50 to 1000 nm, more preferred 50-200 nm, still more preferred 130-170 nm, most preferably about 150 nm.

According to the invention, metallic implants, implants made of metal alloys, plastics, glasses, ceramic implants, composite materials or combinations of these can be used as implants. Examples of preferred implants are catheters, osteosynthesis plates, endoprostheses, external/internal fixateurs, nails, screws and/or wires, heart valves, artificial blood vessels, and shunts, implants for facial/plastic surgery, middle ear implants, and dental implants.

Examples of metals and metal alloys which can be preferably used according to the invention are titanium, steel, iron and/or alloys of steel, iron, titanium, cobalt-chromium base alloys and/or osteosynthesis steel, preferably AISI316L. Particularly preferred are titanium alloys. Among the titanium alloys, TiAl6V4 and TiAl6Nb7 are particularly preferred.

Examples of plastics which can be preferably used according to the invention are polymers such as polyethylene, polypropylene, polytetrafluoroethylene, polyethylene terephthalate, polyamides, polyurethanes, polysiloxanes, polysiloxane elastomers, polyetherether ketone, and polysulfone.

Examples of ceramic materials which can be preferably used according to the invention are aluminum oxide, zirconium oxide, hydroxylapatite, glasses, and glass ceramics.

It is required according to the invention that the metal ions are distributed homogeneously throughout the titanium oxide coating since human cells and bacteria are very sensitive for concentration gradients and therefore a homogeneous effect over the whole area of the coating is not assured if there is a local distribution or concentration, respectively, in the micrometer range. Thus, according to the present invention, homogeneously is intended to mean that the metal ions are essentially present dispersed on a molecular or atomic level and essentially do not form aggregates having a diameter of more than a few nanometers.

A homogeneous distribution of this type can be achieved according to the invention by preparing, for the preparation of the titanium oxide coating on the implant, a coating preparation or suspension, respectively, which is used for the application onto the implant and in which metal ions are dissolved.

The method according to the invention for coating of substances or implants, respectively, comprises the following steps. First, a preparation is prepared as a suspension of low viscosity, a so-called sol, containing an organic solvent, an organometallic titanium oxide precursor as well as optionally water and/or an acid, preferably a mineral peptization agent, and added with metal compounds (metal salts and/or organometallic compounds). According to the invention, sol refers to a colloidal solution in which a solid or liquid substance is dispersed in a liquid medium in a very fine, i.e. essentially in a molecular or atomic, distribution without formation of aggregates. According to the invention, the metal salts and/or metal compounds preferably are completely dissolved in the sol. The sol can also be referred to as a nanosuspension since the metal compounds or ions are dispersed in the nanometer range.

Afterwards, the preparation thus prepared is applied onto an implant and the applied coating is dried. Optionally, a subsequent drying step at 100-1000° C. can be carried out.

By means of the method of the present invention, a titanium oxide coating or an implant having a titanium oxide coating, respectively, has been provided wherein the metal ions having an anti-microbial effect can be dissolved out under physiological conditions whereby an anti-microbial effect, particularly in an area close to the titanium oxide coating can be achieved. After a certain time, when the anti-microbially acting metal ions have been essentially dissolved out, the anti-microbial effect of the coating decreases and the implant is integrated by the body tissue meaning that it is biocompatible. Therefore, the implants according to the invention are particularly useful for implantation into patients. In contrast, known copper-containing materials retain their anti-microbial effect over the complete period of use resulting in a chronic inflammatory reaction and a lack of integration. The present invention enables a defined release of e.g. copper over a period of time which can be adjusted to stop the proliferation of bacteria adhering to the implant without excessive damage to the adhering own cells of the body. Subsequently, however, the coating represents a biocompatible material allowing the growth of the own tissue of the body onto the implant.

Metallic compounds preferably are soluble salts or organometallic compounds or complexes thereof. These are introduced and dissolved in a defined amount in the suspension having a low viscosity or sol, respectively.

This mixture having nearly the viscosity of water is then applied to the substrate which may be accomplished be dip coating, spin coating, blade coating, printing or spraying or other techniques according to the prior art.

Preferably, the titanium oxide precursors contained in the mixture are fourfold coordinated titanium compounds having linear or branched alkyl radicals with a preferred chain length of C2 to C5 bound by oxygen bridges. Instead of or in addition to these unsaturated alkyl radicals (alkenyl radicals) and/or oxygen and/or nitrogen-containing alkyl or alkenyl radicals, respectively, can also be used according to the invention for specific applications such as UV curability wherein these radicals preferably also have 2 to 5 C atoms but also longer alkyl chains up to C-12. Examples of suitable alkyl radicals bound by oxygen bridges are in particular ethyl, n-propyl, isopropyl, n-butyl, isobutyl, n-pentyl and/or isopentyl radicals.

Examples of suitable alkenyl radicals are acrylates, methacrylates or longer alkyl chains or branched alkyl chains carrying double bonds. The preferred chain length for the main chain is C2 to C12, that of the side chains is C2 to C6.

Examples of suitable O-substituted and N-substituted alkyl and/or alkenyl radicals are radicals on the basis of carbon chains meeting the above described requirements, and in addition containing also ether, keto or amino groups.

Examples of titanium oxide precursors which may be used according to the invention are tetrabutoxy titanate, titanium isobutoxy titanate, titanium tetrapropylate, titanium tetraisopropylate, titanium tetraacetyl acetonate, titanium tetraethoxy titanate.

As the organic solvent, linear or branched alcohols with chain lengths of 2 to 8 carbon atoms are preferably used, e.g. ethanol, propanol, isopropyl alcohol, n-butanol, sec-butanol or combinations of the above-mentioned alcohols wherein ethanol and n-butanol are particularly preferred. Other organic solvents which may be used according to the invention are cyclic, aromatic and/or heteroaromatic hydrocarbons or the derivatives thereof, for example cyclopentane, cyclohexane, benzene, toluene, tetrahydrofuran or dioxane, wherein benzene, toluene and/or tetrahydrofuran are particularly preferred. The organic solvent can be selected by those skilled in the art according to the metal salt or organometallic compound used.

Optionally water and/or an acid, preferably a mineral peptization acid, can be contained in the preparation.

Preferably, nitric acid is used as the mineral peptization acid. In addition to or instead of nitric acid, however, other peptization acids can be used such as hydrochloric acid, sulphuric acid, phosphoric acid, or organic acids such as citric acid or acetic acid.

If an acid or peptization acid, respectively, is used, the concentration of the acid or peptization acid, respectively, preferably is 1 to 50 mole % of the titanium oxide precursor employed, preferably 2 to 20 mole %, still more preferably 8 to 10 mole %.

The concentration of the solvent preferably is 5 to 50 times the molar amount of the titanium oxide precursor, more preferably 15 to 40 times, still more preferred 20 to 35 times.

The proportion of the metal compounds preferably corresponds to a cold saturation of the coating solution. Respective dilutions can be performed continuously and are adapted to the application case. Also preferable is to choose the concentration of metal ions in the coating so that the applied and dried and optionally heated titanium oxide coating has a concentration of metal ions of 1-20% by weight, preferably 5 to 15% by weight, still more preferred 10-12% by weight.

The metal salts and/or organometallic compounds used in the coating preparation preferably have mono- to tetravalent metal ions, preferably zinc, mercury, vanadium, aluminium, titanium, chromium, cadmium, tin, lead, nickel and/or cobalt salts, more preferably calcium, magnesium, copper, zinc and/or silver salts. As the counter ions, nitrates, sulfates, carbonates, hydroxides, but preferably acetates and chlorides can be employed. Examples according to the invention are for example copper acetate, copper chloride, silver acetate.

It is possible to achieve according to the present invention that during or after application of the preparation described above, preferably in the form of a sol, onto the substrate the sol transforms into a solidified, deformation resistant but easily deformable system or a gel, respectively, by evaporation the solvent and/or adjusting stoichiometric ratios of the educts wherein the metal ions ate present truly homogeneously dissolved within the solidified system or gel and thus are essentially dispersed on a molecular level. Sol-gel procedures for the coating of materials are known per se, however, not known is the modification thereof according to the present invention for introducing metal ions into the coating which can be eluted.

Subsequently, drying is performed whereafter the coated implants can be directly used. Optionally, also a heat treatment at temperatures of 100 to 1000° C. for about 0.1-3 hours, preferably 0.1-1 hour is carried out which can take place under an oxygen, nitrogen, argon or air atmosphere. This subsequent heat treatment serves for mechanical stabilization or densification, respectively, of the coatings. For example ceramization of the coating can be achieved preferably by heating at about 500° C. In the case of plastic implants preferably heating at lower temperatures is carried out.

The drying step optionally is performed under supercritical conditions, preferably in an autoclave. "Supercritical conditions" as referred to herein is intended to mean a pressure-temperature-time profile at a predetermined autoclave volume wherein by means of reducing the specific density without formation of a phase boundary the solvent used is carried from the liquid into the gaseous state beyond the physically defined critical point and is thereby removed from the layer.

The specific advantages of this method are that the pore structure in the nanometer range which is typical for gels is retained whereby a very high specific surface of the coating is formed. This allows on the one hand to exert an additional influence on the ion release kinetics of the copper ions and on the other hand, by creating a structured porous surface, to bring about a positive influence on the growth of body cells such as osteoblasts or fibroblasts.

Optionally, also a heat treatment at temperatures of 100 to 1000° C. for about 0.1-3 hours, preferably 0.1-1 hour is carried out which can take place under an oxygen, nitrogen, argon or air atmosphere. This subsequent heat treatment serves for mechanical stabilization of the coatings. For example ceramization of the coating can be preferably achieved by heating at about 500° C. In the case of plastic implants preferably heating at lower temperatures is carried out.

By means of the method according to the invention it is possible by dilution or multiple coating, respectively, to precisely adjust the concentration of metal ions, preferably copper and/or silver ions, in the coating. By multiple coatings the anti-microbial effect of the coating can be enhanced since in this case a higher amount of metal ions having an anti-bacterial effect which can be eluted can be provided. A double to fourfold coating is preferred.

According to the invention a multiple coating is prepared by repeating the steps of the preparation of a titanium oxide coating on an implant, i.e. addition of a preparation containing an organic solvent and an organometallic titanium oxide precursor and optionally water and/or an acid with metal salts and/or organometallic compounds to distribute metal ions homogeneously in the preparation, application of the preparation thus prepared onto an implant and drying the applied coating, once or more times so that one or more additional titanium oxide coatings are prepared on the implant. Optionally, heating to 100 to 1000° C. can be performed each time after the above-mentioned steps of the procedure have been carried out.

The concentrations of metal ions are preferably varied in each case so that the one or more additionally applied, dried, and optionally heated coatings have different metal ion concentrations or also different metal ions, respectively wherein particularly preferred the metal ion concentrations are varied in each case to achieve decreasing metal ion concentrations in the coatings from the internal coatings closer to the implant to the external coatings.

The advantage of this process is that the release kinetics and the associated location-specific formation of the coating can be precisely adjusted. Thus it is possible to achieve for example a fast reduction of the germ number directly after implantation by introducing silver into the outermost layer which has a strong bactericidal effect. By an elution of copper from the more internal layers at later times the germ number is kept at a low level without interfering with the growth of cells involved in the integration of the implant in the body.

Also, in case of multiple coating the metal ions are homogeneously distributed in each of the individual coatings.

In the following several examples will be described which, however, are not intended to limit the scope of the invention.

In the examples, reference is made to the following Figures:

FIG. 1 shows the development of the cell number of *S. aureus* ATCC 25923 after 24 h of culture on various material surface.

Figure 2:
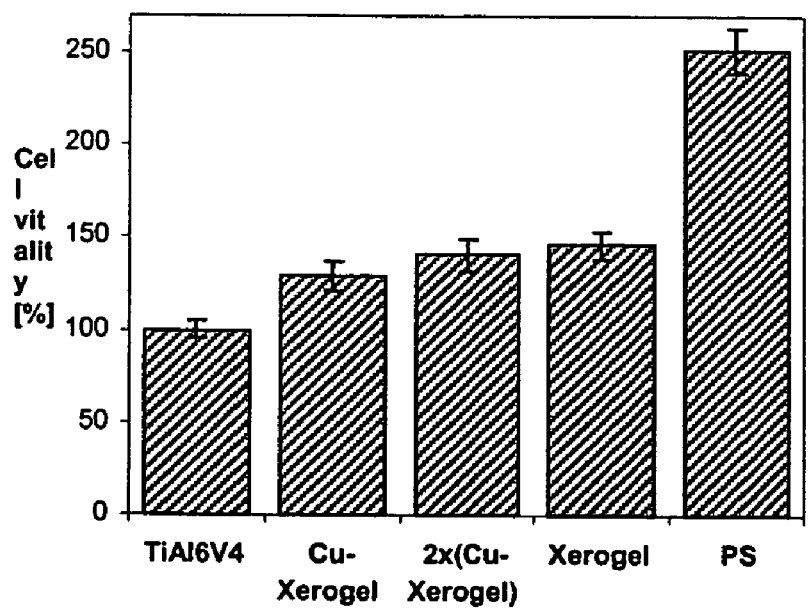
FIG. 2 shows the development of the cell number of mouse fibroblasts (L929) after 24 h of culture on various material surfaces.

FIG. 2 shows the development of the cell number of mouse fibroblasts (L929) after 24 h of culture on various material surfaces.

EXAMPLES

Example 1

Coating 69.5 g of tetrabutoxy titanate were dissolved in 500 g n-butanol at rt and stirred for 2 h under inert gas conditions. Then copper acetate is added in portions up to cold saturation. The supernatant is drawn off the sediment and used as the coating.

The coating is prepared by immersing the test specimen TiAl6V4, glass or plastic with a take-up velocity of 1.5 mm/s. Afterwards, drying is performed for 1 h at room temperature and the coating is ceramized at 500° C. for 10 min.

If plastic is coated the ceramization step is omitted and instead curing for 1 h at 120° C. is carried out after drying.

Example 2

Demonstration of the Mode of Action

To demonstrate the mode of action of the anti-bacterial coating studies were performed using clinically relevant bacterial strains (*Staphylococcus aureus*: ATCC25923, MRSA27065, and *Staphylococcus epidermidis*: ATCC35984, RP62a, SE 183) on the one hand and connective tissue cells (L292, mouse fibroblasts) and fetal osteoblasts (MC3T3-E1)) on the other hand. TiAl6V4 plates (14.5 mm diameter, 1 mm thickness) with an anti-bacterial coating according to the invention served as the sample material. For direct comparison the experiments were performed with cells and bacteria in the same cell culture medium (culture medium: 90% RPMI 1640 (=2.05 mM glutamine-containing serum), 10% FCS (fetal calf serum); incubation: 24 h, 37° C., 5% CO2, static culture, darkness)

Cell lines: MC3T3-E1 (mouse osteoblasts)
L292 (mouse fibroblasts)
24-well culture dishes, polystyrene
inoculum: 120,000 cells/ml and well, 1 g phase, passage 6
cell proliferation: trypsinization (300 µl of trypsin EDTA) for a period of 8 minutes in an agitated incubator at 37° C., the enzyme reaction is stopped with 700 µl of culture medium.

Determination of the cell number by means of Coulter counter.

Bacterial strains (ATCC25923, MRSA27065, ATCC35984, RP62a, SE 183)

All experiments were carried out corresponding to the cell tests inoculum: 100,000 cells per ml and well Detachment of adhering microorganisms was performed by means of ultrasound, the number of bacteria was determined quantitatively after diluting by counting the "colony-forming units (cfu)" after 24 hours at 37° C. on nutrient media (Müller-Hinton agar plates), and the undiluted germ number was calculated. Only the vital bacteria were counted since dead or inactivated germs do not form cfus.

FIG. 1 shows the development of the cell number of *S. aureus* ATCC 25923 after 24 h of culture on various material surfaces.

TiAl6V4: reference, pure alloy
Cu-Xerogel: TiAl6V4 provided with a single copper-containing titanium oxide coating according to the invention as in ex. 1
2x Cu-Xerogel: TiAl6V4 provided with a double copper-containing titanium oxide coating according to the invention
Xerogel: pure titanium oxide coating with addition of copper FIG. 2 shows the development of the cell number of osteoblast-like cells (MC3T3-E1) after 24 h of culture on various material surfaces:

TiAl6V4: reference, pure alloy
Cu-Xerogel: TiAl6V4 provided with a single copper-containing titanium oxide coating according to the invention as in ex. 1
2x Cu-Xerogel: TiAl6V4 provided with a double copper-containing titanium oxide coating according to the invention
Xerogel: pure titanium oxide coating with addition of copper
PS: polystyrene as the control It can be seen from FIG. 2 that in the case of a single copper coating according to the invention the cell number of fibroblasts increases compared to the metal alloy. In the case of a copper-containing double layer (corresponding to twice the amount of copper in the system) the cell numbers within the error ranges are even on the same level as in the case of the single Xerogel-coated alloy.

It can be clearly seen for the bacterial strains (FIG. 1) that already with a single coating according to the invention the cell number decreases by two orders of magnitude. The cell number is even more clearly decreased with a double coating.

Also, a fourfold coating according to the invention results in a reduction in the cell number of 6 orders of magnitude which corresponds to sterilisation in a microbiological sense.

A comparable reduction of the bacterial growth was achieved in the incubation solution surrounding the coated metal test pieces. This makes clear that an elution of copper ions into the culture medium in fact occurs and the antibacterial effect is not merely a surface effect.

REFERENCES

[1] Illingworth B., Bianco R. W., Weisberg S., In vivo efficacy of silver-coated fabric against *Staphylococcus epidermidis*, J Heart Valve Dis 1 (2000) 135-41.
[2] Darouiche R. O., Anti-infective efficacy of silver-coated medical prostheses, Clin Infect Dis 6 (1999) 1371-7.

[3] Ambrosius W. T., Harris V. J., Snidow J. J., Tunneled hemodialysis catheters: use of a silver-coated catheter for prevention of infection—a randomized study, Radiology 2 (1998) 491-6.

[4] Grzybowski J., Trafny E. A., Antimicrobial properties of copper-coated electro-conductive polyester fibers, Polim Med 29 (1999) 27-33.

[5] Cooney T. E., Bactericidal activity of copper and noncopper paints, Infect Control Hosp Epidemiol 16 (1995) 444-50.

[6] Komatsu Y., Sadakata I., Ogra Y., Suzuki K. T., Excretion of copper complexed with thiomolybdate into the bile and blood of LEEC rats, Chem Biol Interact 124 (2000) 217-31.

[7] Jokinen M., Pätsi M., Rahiala H., Peltola T., Ritala M., Rosenholm J. B., Influence of sol and surface properties on in vitro bioactivity of sol-gel-derived TiO2 and TiO2-SiO2 films deposited by dip-coating method, J. Biomed. Mater. Res. 42 (1998) 295-302.

[8] Heidenau F., Schmidt H., Stenzel F., Ziegler G., Sol-Gel-Derived Titania with Gradient Porosity, Key. Eng. Mater. 161-163 (1999) 115-116.

[9] Feng Q. L., Cui F. Z., Kim T. N., Kim J. W., Ag-substituted hydroxyapatite coatings with both antimicrobial effects and biocompatibility, J Mater Sci Lett 18 (1999) 559-61.

[10] Shirkhanzadeh M., Azadegan, M., Formation of carbonate apatite on calcium phosphate coatings containing silver ions, J Mater Sci: Mater Med 9 (1998) 385-91.

[11] Gristina A. G., Biomaterial-centered infection: Microbial adhesion versus tissue integration, Science 237 (1987) 1588-95.

[12] Dunne W. M. Jr., Mason E. O. Jr., Kaplan S. L., Diffusion of rifampin and vancomycin through a *Staphylococcus epidermidis* biofilm. Antimicrob. Agents Chemother. 37 (1993) 2522-6.

[13] Darouiche R. O., Dhir A., Miller A. J., Landon G. C., Raad I. I., Musher D. M., Vancomycin penetration into biofilm covering infected prostheses and effect on bacteria, J. Infect. Dis. 170 (1994) 720-3.

The invention claimed is:

1. A method for the preparation of a titanium oxide coating on an implant comprising the steps of:
   a) forming a preparation comprising an organic solvent, an organometallic titanium oxide precursor and metal ions as metal salts and/or organometallic compounds, wherein the preparation is a sol in which the metal ions are homogeneously dispersed and dissolved, and wherein the metal ions are selected from the group consisting of zinc, mercury, vanadium, aluminum, chromium, cadmium, tin, lead, nickel, cobalt, calcium, magnesium, copper, and silver;
   b) applying the preparation prepared in a) onto an implant to form a coating;
   c) drying the coating, wherein the metal ions in the coating exert an anti-microbial or antibacterial effect under physiological conditions.

2. The method according to claim 1 characterized in that after said step c) heating is concluded to 100 to 1000° C.

3. The method according to claim 1, characterized in that the implant is a metal, metal alloy, a glass, a ceramic, a plastic, a composite material, or a bone implant.

4. The method according to claim 1 characterized in that said implant is a catheter, an osteosynthesis plate, an endoprosthesis, an external fixateur, an internal fixateur, a nail, a screw, a wire, a heart valve, an artificial blood vessel, a shunt, an implant for facial/plastic surgery, a middle ear implant, or a dental implant.

5. The method according to claim 3 characterized in that the implant is a metal or metal alloy selected from titanium, steel, iron, a steel alloy, an iron alloy, a titanium alloy, and a CoCr alloy.

6. The method according to claim 5 characterized in that the implant is a titanium alloy, a CoCr alloy or an osteosynthesis steel.

7. The method according to claim 3 characterized in that the implant is a plastic selected from polyethylene, polypropylene, polytetrafluoroethylene, polyethylene terephthalate, a polyamide, a polyurethane, a polysiloxane, a polysiloxane elastomer, a polyetherether ketone, a polysulfone, and a mixture thereof.

8. The method according to claim 1 characterized in that the organic solvent is selected from a linear or branched alcohol with a chain length of 2 to 8 carbon atoms, a cyclic hydrocarbon, an aromatic hydrocarbon, or a heteroaromatic hydrocarbon.

9. The method according to claim 1 characterized in that the organometallic titanium oxide precursor is fourfold coordinated titanium having linear or branched alkyl and/or alkenyl radicals bound by oxygen bridges wherein the alkyl and/or alkenyl radicals can have O and/or N atoms substituted or within the chain.

10. The method according to claim 1, wherein the preparation further comprises water and/or an acid.

11. The method according to claim 1 characterized in that the metal ions are selected from zinc, mercury, vanadium, aluminium, titanium, chromium, cadmium, tin, lead, nickel, cobalt, calcium, magnesium, copper, zinc and silver ions, and a mixture thereof.

12. The method according to claim 1 characterized in that the metal ion concentration in step a) is selected to give a metal ion concentration of 1-20% by weight in the coating.

13. The method according to claim 1 characterized in that step b) is carried out by dip coating, spin coating, blade coating, printing or spraying.

14. The method according to claim 1 characterized in that the preparation of step a) is applied in a coating thickness that the coating thickness of a single coating after drying and optionally heating is 50-1000 nm.

15. The method according to claim 1 characterized in that said sol transforms into a gel during or after step b).

16. The method according to claim 1 characterized in that the steps a)-c) of claim 1 are repeated one or more times to generate one or more additional titanium oxide coatings on the implant wherein each of the coatings can optionally be heated after step c) to 100 to 1000° C.

17. The method according to claim 16 characterized in that the metal ion concentration is varied in step a) to achieve different concentrations of metal ions in the original coating and the one or more additionally applied, dried and optionally heated coatings.

18. The method according to claim 17 characterized in that the metal ion concentration is varied in step a) to achieve concentrations of metal ions that decrease from the internal coatings close to the implant to the external coatings.

19. The method according to claim 1 characterized in that drying of the coating applied in step c) is performed under supercritical conditions.

20. The method according to claim 16 characterized in that the individually applied coatings contain different metal ions.

21. The method according to claim 16 characterized in that the metal ions are copper ions and/or silver ions.

22. An implant having a titanium oxide coating prepared according to claim 1.

23. The implant according to claim 22 characterized in that the metal ions contained in the coating can be dissolved out of the coating into the surrounding medium under physiological conditions.

24. The implant according to claim 22 characterized in that the layer thickness of a single titanium oxide coating is 50-1000 nm.

25. The implant according to claim 22 characterized in that the implant comprises a plurality of titanium oxide coating layers comprising metal ions homogeneously dispersed in each coating.

26. The implant according to claim 22 characterized in that the metal ions are contained in the titanium oxide coating in a concentration such that the coating initially has an antibacterial effect and later is biocompatible.

27. The implant according to claim 22 characterized in that the metal ion concentration in the titanium oxide coating is 1-20% by weight.

28. The implant according to claim 22 characterized in that the metal ions contained in the titanium oxide coating are copper ions, silver ions, or a mixture thereof.

29. A method of implanting a coated implant within a patient, comprising
   providing an implant according to claim 22; and
   implanting the implant within the body of the patient.

30. The method according to claim 10 characterized in that the preparation comprises an acid selected from nitric acid, hydrochloric acid, sulphuric acid, phosphoric acid, an organic acid and a mixture thereof.

\* \* \* \* \*